United States Patent [19]

Heit et al.

[11] Patent Number: 5,287,632
[45] Date of Patent: Feb. 22, 1994

[54] SUPERCRITICAL FLUID AND NEAR CRITICAL GAS EXTRACTION OF ORGANIC SOLVENTS FROM FORMED ARTICLES

[75] Inventors: Lawrence B. Heit, Basel, Switzerland; James M. Clevenger, Glen Gardner, N.J.

[73] Assignee: Ciba-Geigy Corporation, Ardsley, N.Y.

[21] Appl. No.: 557,283

[22] Filed: Jul. 24, 1990

Related U.S. Application Data

[63] Continuation-in-part of Ser. No. 388,095, Jul. 31, 1989, abandoned.

[51] Int. Cl.$^5$ ............................................. F26B 3/00
[52] U.S. Cl. ............................................. 34/9; 34/32
[58] Field of Search ............... 34/5, 15, 17, 19, 22, 34/12, 9, 32; 426/601

[56] References Cited

U.S. PATENT DOCUMENTS 4,326,525  4/1982  Swanson et al. .
4,731,208  3/1988  Nakajima et al. .
4,943,403  7/1990  Miyashita et al. .
4,970,235  11/1990  Traitler et al. ............... 426/601 X

FOREIGN PATENT DOCUMENTS 0206685 12/1986 European Pat. Off. .

OTHER PUBLICATIONS

Food Technology, Jun. 1986, pp. 66-69.
Val Krukonis, Supercritical Fluid Franctionation-an Alternative to Molecular Distillation Spring 1983.
Reviews in Chemical Engineering, Supercritical Fluid Extraction, vol. 1, No. 2 1983.

Primary Examiner—Henry A. Bennet
Attorney, Agent, or Firm—Irving M. Fishman; Karen G. Kaiser

[57] ABSTRACT

Disclosed is a method of removing residual organic solvents from formed compressed articles such as tablets comprised of subjecting the organic solvent laden compressed article to a supercritical fluid or near critical gas whereby residual solvent is transferred from the solvent laden solid article to the supercritical fluid or near critical gas and separating the residual solvent depleted compressed article from the solvent enriched supercritical fluid or near critical gas.

20 Claims, No Drawings

SUPERCRITICAL FLUID AND NEAR CRITICAL GAS EXTRACTION OF ORGANIC SOLVENTS FROM FORMED ARTICLES

This application is a continuation-in-part of Ser. No. 07/388,095 filed Jul. 31, 1989 now abandoned.

FIELD OF THE INVENTION

The invention relates to a process for the extraction of residual solvent from formed compressed articles such as tablets. The process consists of exposing the formed compressed articles to an inert phase of a fluid under supercritical conditions or to an inert phase of a gas under near-critical conditions. The solvent is transferred from the formed compressed article to the inert phase.

BACKGROUND OF THE INVENTION

Many processes for the removal of volatile solvents from bulk masses are known. Air drying is often unsatisfactory for various reasons. As solvent poor dry air passes over a solvent rich area, a fraction of the solvent evaporates when the equilibrium is established. As the solvent enriched air is removed (by normal air currents or otherwise), it is replaced with additional solvent poor air and more solvent is given up. The process continues until equilibrium is reached and all or most of the solvent has been removed. Under certain conditions (i.e. high solvent volatility, minimal solvent/substrate affinity, high diffusion rates, etc.) such a process may take place rapidly within minutes, while in other cases this solvent loss is inhibited due to low solvent volatility, strong solvent/substrate binding, or low diffusion rates. In many cases the evaporation rate is unacceptably low.

Many alternative processes and improvements are known. For example, heat is applied to accelerate the evaporation rate, pressure reductions are applied as well as combination thereof. Liquid solvent exchange (leaching) is also used. In this process the solid material containing the residual solvent is exposed to another liquid which has less solubility for the solid material from which the residual solvent is to be removed, but a greater solubility for the residual solvent. The residual solvent is then transferred from the solid material to the other liquid and the liquid enriched in solvent is then separated from the solid material.

The removal of solvent can be extremely difficult from a formed compressed article such as uncoated or coated tablets. The removal from coated tablets requires the complete evaporation from the film coating and the covered compressed tablet core.

The increasing demand for extremely low solvent content in pharmaceutical dosage forms such as coated tablets may mandate that none of the foregoing conventional solvent removal processes is satisfactory.

The extraction of residual solvents by exposure of the article to be made solvent free to an inert phase of a fluid under supercritical conditions or to an inert phase of a gas under near-critical conditions is another known process that has been applied to solids such as bulk masses. Especially in the food industry this method has been applied to remove caffeine from green coffee or nicotine and liquid admixtures from tobacco. This method is applicable wherever esthetic qualities associated with the solvent free article, such as shape, color, surface characteristics or physical appearance are of little concern.

It has not been attempted before to expose solid articles such as formed compressed tablets, which also contain residual solvent, to fluids under supercritical conditions or gases under near-critical conditions.

OBJECTS OF THE INVENTION

It is an object of the invention to provide an improved process to remove residual solvent from a formed compressed article such as granulates or coated or uncoated tablets without significantly altering or deteriorating the appearance and/or stability of that solid article as well as pharmacological properties thereof such as release rates.

It is a further object of the invention to recover any residual solvent from the solid article.

SUMMARY OF THE INVENTION

The present invention relates to a process for extracting residual solvent from a solid article which consists of exposing that solid article to an inert phase of a fluid under supercritical or of a gas under near-critical conditions, transferring a portion of the residual solvent from the solid article to the inert phase of the fluid or gas and removing the inert phase enriched with solvent from the solid article depleted of solvent, characterized in that the residual solvent is extracted from a formed compressed article.

DETAILED DESCRIPTION OF THE INVENTION

The term residual solvent defines water or organic solvents that are present as contaminants in solid articles such as uncoated or coated tablets due to the presence of those solvents in a precursory step such as preparation of wet granulates or coating from organic liquids. Due to their toxicity, the presence of residual organic solvents such as methanol or methylene chloride is especially undesirable.

The term solid article defines formed compressed articles from which the residual solvent is extracted. This term preferably includes: coated or uncoated tablets, granules or pellets or suppositories. Preferred are the above-mentioned compressed articles obtainable according to standard pharmacological methods such as tablets from so-called wet granulation. Especially preferred are coated tablets, especially those known in the art under the term oral oral osmotic system.

Most preferably, the formed compressed article is a firm coated tablet. The most preferred type of such tablet is a film coated tablet of the type known as oral osmotic (OROS ™ Alza) dosage forms—a number of such dosage forms are described in U.S. Pat. Nos. 4,326,525, 4,439,195, 4,455,143 and 3,916,899, etc. Some of those dosage forms are commercially available.

Preferably, the film coating in the coated tablets is selected from cellulose ethers and esters such as sodium carboxymethylcellulose, ethylcellulose, methylcellulose, hydroxypropylcellulose, hydroxypropyl methylcellulose, cellulose acetates including cellulose acetate phthalate, hydroxypropyl methylcellulose phthalate, gelatin, pharmaceutical glaze, polyethylene glycol, polyvinyl acetate phthalate, sucrose, carnauba wax, microcrystalline wax, acrylic and/or methacrylic ester and acrylic and/or methacrylic acid copolymers, other vinylic polymers and copolymers such as polyvinylpyrrolidone, with or without plasticizers typically selected from castor oil, diacetylated monoglycerides, diethyl phthalate, glycerin, mono- and di-acetylated monoglycerides, polyethylene glycol, propylene glycol, and triacetin, citrate esters, phthalate esters, mineral oil and vegetable oils, and further with or without coloring agents, and more preferably cellulose ethers, cellulose acetates, vinyl polymers, acrylic esters and copolymers, polyglycols, with or without coloring agents, and most preferably cellulose ethers, cellulose acetates, polyglycols, acrylic esters and copolymers with or without coloring agents. These coating agents are applied to the tablet cores from organic solutions according to methods known in pharmaceutical technology, e.g. spraying methods, e.g. in a fluid bed or in a spray pan.

An inert phase of a fluid under supercritical conditions contains a pure component or mixture of components, above its critical temperature and critical pressure. For a pure component, there is one specific temperature above which the application of pressure will not yield a condensed (liquid or solid) phase. That temperature defines the critical temperature for that component. The pressure at the critical temperature which will first produce a condensed phase is referred to as the critical pressure. The critical temperature and critical pressure define the critical point. While the critical point is unique for each pure component, the critical point of a mixture is dependent on the composition of the mixture and varies with the molar fraction of each component.

Fluids under supercritical conditions exhibit properties similar to both liquids and gases. For example, so-called supercritical fluids have densities and solvating power similar in magnitude to those observed in liquids while exhibiting diffusion rates associated with gases. Another property associated with supercritical fluids is that small changes in temperature and/or pressure result in considerable changes in properties such as density or solvating potential. These properties are varied by varying temperature and/or pressure.

An inert phase of a gas under near-critical conditions contains a gas or mixture of gases where the temperature is typically slightly above the critical temperature but the pressure is slightly lower than the critical pressure or where the temperature is slightly below the critical temperature and the pressure is slightly below the liquification pressure at that temperature.

A suitable so-called supercritical fluid or near-critical gas is inert to the solid article from which the solvent is removed. The fluid or gas is especially inert to the active agent present in the solid article and also inert to the additives and carrier materials as contained therein. It is mandatory that no significant chemical reaction occurs with any of the ingredients of the solid article. Physical appearance such as shape, hardness, friability or color is preserved during the process.

A suitable so-called supercritical fluid or near-critical gas is any liquid or gas which can be subjected to an elevation of temperature and/or pressure above or near its critical point without decomposing and which such temperature and pressure will not adversely affect or decompose the solid article. Typical supercritical fluids, and near-critical gases, with their critical temperatures and pressures, include, but are not limited to:

a) ammonia (132.5° C., 112.5 atm), sulfur hexafluoride (45.6° C., 37.7 atm), argon (−122.3° C., 48 atm), carbon dioxide (31° C., 72.9 atm), deuterium (−234.8° C., 16.4 atm), helium (−267.9° C., 2.26 atm), hydrogen (−239.9° C., 12.8 atm), krypton (−63.8° C., 54.3 atm), neon (−228.7° C., 26.9 atm), nitrogen (−147° C., 33.5 atm), nitrous oxide (36.5° C., 71.7 atm), and xenon (16.6° C., 58 atm); and b) chlorodifluoromethane (96° C., 48.5 atm), fluoromethane (44.6° C., 58 atm), methane (−82.1° C., 45.8 atm), bromotrifluoromethane (67° C., 50.3 atm), chlorotrifluoromethane (28.85° C., 38.2 atm), dichlorodifluoromethane (111.5° C., 39.6 atm), $CF_4$ (−45.7° C., 41.4 atm), ethyne (35.5° C., 61.6 atm), ethene (9.9° C., 50.5 atm), fluoroethane (102.16° C., 49.6 atm), ethane (32.2° C., 48.2 atm), methylether (127° C., 52.6 atm), propadiene (120° C., 43.6 atm), propyne (127.8° C., 52.8 atm), propane (96.8° C., 42 atm), n-butene (146° C., 39.7 atm), i-butane (135° C., 36 atm), perfluoro-n-butane (113.2° C., 23 atm).

Of these gases or liquids those having a critical temperature below about 150° C. are preferred, while those with a critical temperature below about 100° C. are more preferred. Highly preferred are $CO_2$, argon, helium, neon, nitrous oxide, nitrogen, and methane; more highly preferred are nitrous oxide and $CO_2$; most highly preferred is $CO_2$.

The near critical gas is suitably a gas within the range of about 80% of to just below the critical temperature, preferably at least 85% of, more preferably at least 90% of, and most preferably at least 95% of the critical temperature and greater than 90% to less than 100% of its liquification pressure at that temperature or a temperature at or in excess of the critical temperature and at a pressure which is about 80% to just below the critical pressure, preferably at least 85% of, more preferably at least 90% of, most preferably at least 95% the critical pressure. For purposes of this paragraph, the temperature is expressed in °K. rather than in °C., so that for $CO_2$ with a critical temperature of 31° C., 80% of the critical temperature is 263.2° K. (−34.8° C.).

An advantageous set of conditions for use of $CO_2$ in the present invention is at 20° to 65° C., more preferably about 25° C. to 65° C. and 40 to 1000 bar, preferably about 40 to 100 bar. The length of time for which the formed compressed solid article should be exposed to the extracting medium depends on the solvent to be extracted, eventual coatings of tablets which must be permeated and the extraction medium used.

The extraction conditions can be maintained for a period from under 10 minutes to in excess of 24 hours to assure removal of the solvent. Preferably, however the extraction conditions are maintained from about 15 minutes to about 16 hours, more preferably from about 30 minutes to about 12 hours yet more preferably from about 4 hours to about 8 hours.

Preferred solvents which are extractable from the formed compressed articles by the present invention include: water and organic compounds with a vapor pressure greater than 1 mm Hg at 20° C.; more preferred are acetone, ethanol, amylene hydrate, benzyl benzoate, butyl alcohol, carbon tetrachloride, chloroform, corn oil, cottonseed oil, glycerin, isopropyl alcohol, methyl alcohol, methylene chloride, methyl isobutyl ketone, mineral oil, peanut oil, polyethylene glycol, polypropylene glycol, propylene glycol, sesame oil, and most preferred are methyl alcohol, methylene chloride, acetone, and water.

The residual solvent remaining after treatment by the instant invention is significantly less than that which was present prior to such treatment, at least less than 50%, preferably less than 30%, till more preferably less than 20% and most preferably from less than about 7% of the residual solvent content prior to such treatment.

The solvent content of the formed compressed article is reduced to ranges from about 1.0% to 0.0001%, especially 0.01% to 0.001% of the weight of the article. This extremely low solvent content obtained by the method according to the present invention exceeds the requirements for pharmaceutical production as expressed by the standardized Good Manufacturing Practise (GMP).

If desired, the so-called supercritical fluid or near-critical gas enriched in the solvent can be separated from the formed compressed article in a manner so as to recover the solvent therefrom. Typically, mere reduction of pressure below the critical point is all that is necessary, although any method known in the art for separating a compound from a supercritical fluid or near-critical gas may be employed.

The invention especially relates to a process for extracting organic residual solvent from a solid article which consists of exposing that solid article to an inert phase of carbon dioxide or nitrous oxide under near-critical or supercritical conditions, transferring a portion of the organic solvent from the solid article to the inert phase and removing the inert phase enriched with organic solvent from the solid article depleted of solvent, characterized in that the organic solvent is extracted from coated tablets.

This preferred process variant is performed according to the preferred embodiments mentioned above.

The invention will be more clearly understood in the context of the following Examples which are exemplary only and not limiting the invention.

EXAMPLE 1

108.6 kg of metoprolol fumarate powder and 5.4 kg of hydroxypropyl methylcellulose are blended together. The mixture is then granulated with 17.9 kg of a 65/35 weight/weight (w/w) solution of SD 3A anhydrous ethanol and water in which 5.4 kg povidone has been dissolved. The wet granulation is then milled using a Fitzpatrick comminuting machine. The mixture is then regranulated with 8.7 kg of a 65/35 (w/w) solution of SD 3A anhydrous ethanol and water and remilled. The wet granules are dried for approximately 16 hours at 40° C. The dried granules are then milled and blended with 3.4 kg of magnesium stearate. The blended mixture is then compressed into 430 mg tablet cores.

A 5 mg per tablet, hydroxypropyl methylcellulose coating is applied to the tablet cores by spraying a 63/37 w/w mixture of methylene chloride and methanol containing 2.5% by weight hydroxypropyl methylcellulose. A 40 mg per tablet laminate containing 85% cellulose acetate, 11% hydroxypropyl methylcellulose, and the remainder being polyethylene glycol is then similarly applied using a 80/20 w/w solvent mixture of methylene chloride and methanol. The coating operations are performed in a Glatt Wurster Coater ® (fluid bed). The coated tablets are then drilled to result in a bore of about 0.3 mm diameter connecting the inner tablet core with the outside atmosphere.

As a result of the spray coating operation, the coated tablets contain about 0.4% methylene chloride and 0.16% methanol by weight. The tablets are then exposed to $CO_2$ at 111 bar at 60° C. for 8 hours. The solvent content of the film coated tablets after extraction is about 0.005% methylene chloride and 0.01% methanol by weight.

The experimental apparatus used is a Milton Roy Supercritical Extraction Screener which essentially consists: one—160 ml per hour high pressure piston pump, one—250 ml bottom feed extraction vessel with temperature controller and heating mantel, two—pressure'step down'vessel (not essential for this application), and a final dry ice trap. Various valves, pressure regulators and valves are also required to maintain the desired extraction pressure. The analysis of the solvent content is performed by gas chromatography.

EXAMPLE 2

Using essentially the same method described in Example 1 to produce the tablet cores, 107.7 kg of metoprolol fumarate is granulated with 12.6 kg of povidone in a 65/35 weight/weight (w/w) solution of SD 3A anhydrous ethanol and water. After the milling and drying steps, 3.3 kg of magnesium stearate is blended with the granules and the mixture is then compressed into 190 mg tablet cores.

Using essentially the same method described in Example 1 to coat the tablet cores (except only one coating is applied), a 21 mg per tablet laminate is applied containing, 84% cellulose acetate, 8% a 80/20 w/w solvent mixture of methylene chloride and methanol. The coated tablets are then drilled to result in a bore of about 0.3 mm diameter connecting the inner tablet core with the outside atmosphere.

As a result of the spray coating operation, the coated tablets contain about 0.76% methylene chloride and 0.44% methanol by weight. The tablets are then exposed to $CO_2$ at 208 bar at 50° C. for 4.5 hours in a Milton Roy Supercritical Extraction Screener. The solvent content of the film coated tablets after extraction is about 0.095% methylene chloride and 0.11% methanol by weight.

EXAMPLE 3

Using film coated tablets prepared in the same manner as in Example 2, the methylene chloride and methanol content was reduced from approximately 0.23% and 0.10% by weight, respectively, to approximately 0.06% methylene chloride and 0.05% methanol by weight, by exposing the tablets to $CO_2$ at 49 bar at 21° C. for 8 hours in a Milton Roy Supercritical Extraction Screener.

EXAMPLE 4

36.0 kg of dextromethorphan-hydrobromide, 6.3 kg of hydroxypropyl methylcellulose, 89.1 kg mannitol, and 1.35 kg stearic acid are blended together. The mixture is then granulated with ca. 16.0 kg of a 50/50 weight/weight (w/w) solution of SD 3A anhydrous ethanol and water in which 0.036 kg FD&C Red #3 has been dissolved. The wet granulation is then milled using a Fitzpatrick comminuting machine. The wet granules are dried for approximately 16 hours at 40° C. The dried granules are then milled and blended with 0.9 kg of magnesium stearate and 1.35 kg stearic acid. The blended mixture is then compressed into 75 mg tablet cores.

A 7.2 mg per tablet coating consisting of 82% cellulose acetate and 18% polyethylene glycol is applied to the tablet cores by spraying a 63/37 w/w mixture of methylene chloride and methanol containing 3% by weight dissolved solids. A 12.5 mg per tablet laminate containing 80% dextromethorphan-hydrobromide and 20% hydroxypropyl methylcellulose is then similarly applied using a 63/37 w/w solvent mixture of methylene chloride and methanol. A third laminate (2.2 mg per tablet) laminate containing 73% hydroxypropyl methylcellulose and 27% coloring agent is then similarly applied using a 63/37 w/w solvent mixture of methylene chloride and methanol. The coating operations are performed in a Glatt Wurster Coater ® (fluid bed). A portion of the coated tablets are then drilled to result in a bore of about 0.3 mm diameter connecting the inner tablet core with the outside atmosphere.

As a result of the spray coating operation, the coated tablets contain about 0.24% methylene chloride and 0.08% methanol by weight. Both the drilled and undrilled tablets are then exposed to $CO_2$ at 111 bar at 40° C. for 8.0 hours in a Milton Roy Supercritical Extraction Screener. The solvent content of both the drilled and undrilled film coated tablets after is less than 0.005% methylene chloride and 0.005% methanol by weight.

EXAMPLE 5

102.9 kg of phenylpropanolamine-hydrochloride and 23.0 kg of hydroxypropyl methylcellulose are blended together. The mixture is then granulated with ca. 17.8 kg of a 67/33 weight/weight (w/w) solution of SD 3A anhydrous ethanol and water. The wet granulation is then milled using a Fitzpatrick comminuting machine. The wet granules are dried for approximately 16 hours at 40° C. The dried granules are then milled and blended with 1.3 kg stearic acid. The blended mixture is then compressed into 80 mg tablet cores.

A 6.5 mg per tablet coating consisting of 90% cellulose acetate and 10% hydroxypropyl methylcellulose is applied to the tablet cores by spraying a 63/37 w/w mixture of methylene chloride and methanol containing 3% by weight dissolved solids. A 12.5 mg per tablet laminate containing 80% phenylpropanolamine-hydrochloride and 20% hydroxypropyl methylcellulose is then similarly applied using a 63/37 w/w solvent mixture of methylene chloride and methanol. A third laminate (2.3 mg per tablet) laminate containing 70% hydroxypropyl methylcellulose and 30% coloring agent is then similarly applied using a 63/37 w/w solvent mixture of methylene chloride and methanol. The coating operations are performed in a Glatt Wurster Coater ® (fluid bed). A portion of the coated tablets are then drilled to result in a bore of about 0.3 mm diameter connecting the inner tablet core with the outside atmosphere.

As a result of the spray coating operation, the drilled coated tablets contain about 0.65% methylene chloride and 0.61% methanol by weight and the undrilled coated tablets contain about 0.74% methylene chloride and 0.71% methanol by weight. Both the drilled and undrilled tablets are then exposed to $N_2O$ at 111 bar at 40° C. for 8.0 hours in a Milton Roy Supercritical Extraction Screener. The methylene chloride content of both the drilled and undrilled film coated tablets after extraction is less than 0.01% methylene chloride by weight. The methanol content of the drilled and undrilled film coated tablets after extraction is reduced to approximately 0.28% and 0.30% by weight, respectively.

EXAMPLE 6

Using film coated tablets prepared in the same manner as in Example 5, the drilled coated tablets contain about 0.55% methylene chloride and 0.52% methanol by weight and the undrilled coated tablets contain about 0.62% methylene chloride and 0.59% methanol by weight. Both the drilled and undrilled tablets are then exposed to $CO_2$ at 111 bar at 50° C. for 8.0 hours in a Milton Roy Supercritical Extraction Screener. The solvent content of both the drilled and undrilled film coated tablets after extraction is reduced to approximately 0.01% methylene chloride and 0.18% methanol by weight.

We claim:

1. A process for extracting residual solvent from a solid article selected from the group consisting of capsules and film coated tablets, said process consisting of exposing that solid article to an inert phase of a fluid under supercritical conditions, transferring a portion of the residual solvent from the solid article to the inert phase of the fluid and removing the inert phase enriched with solvent from the solid article depleted of solvent, wherein said film coated tablets have a film coating comprising a film-forming member selected from the group consisting of cellulose ethers, cellulose esters, gelatin, pharmaceutical glaze, polyethylene glycol, polyvinyl acetate phthalate, sucrose, carnauba wax, microcrystalline wax, (meth)acrylic acid/(meth)acrylic ester copolymers, and other vinylic polymers and copolymers.

2. A process according to claim 1, characterized in that the residual solvent is extracted from film coated tablets.

3. A process according to claim 2, characterized in that the residual solvent is extracted from oral osmotic systems.

4. A process according to claim 3, characterized in that the residual solvent is extracted from oral osmotic systems containing metoprolol fumarate, dextromethorphan hydrobromide or phenylpropanolamine hydrochloride.

5. A process according to any one of claim 1, characterized in that organic solvents are extracted.

6. A process according to claim 5, characterized in that methylene chloride and/or methanol are extracted.

7. The process of claim 1 wherein said solid article is a film coated tablet and said inert phase of fluid under supercritical conditions is an inert phase of a material selected from the group consisting of carbon dioxide and nitrous oxide.

8. A process according to claim 7, characterized in that the organic solvent is extracted from tablets coated with cellulose esters.

9. A process according to claim 7, characterized in that the organic solvent is extracted from oral osmotic systems coated with cellulose esters.

10. A process for extracting residual solvent from a solid article selected from the group consisting of capsules and film coated tablets, said process comprising exposing that solid article to an inert phase of a fluid under supercritical conditions, transferring a portion of the residual solvent from the solid article to the inert phase of the fluid and removing the inert phase enriched with solvent from the solid article depleted of solvent, wherein said film coated tablets have a film coating comprising a film-forming member selected from the group consisting of cellulose ethers, cellulose esters, gelatin, pharmaceutical glaze, polyethylene glycol, polyvinyl acetate phthalate, sucrose, carnauba wax, microcrystalline wax, (meth)acrylic acid/(meth)acrylic ester copolymers and other vinylic polymers and copolymers.

11. A process for extracting residual solvent from a solid article selected from the group consisting of capsules and film coated tablets, said process consisting of exposing that solid article to an inert phase of a gas under near-critical conditions, transferring a portion of the residual solvent from the solid article to the inert phase of the gas and removing the inert phase enriched with solvent from the solid article depleted of solvent, wherein said film coated tablets have a film coating comprising a film-forming member selected from the group consisting of cellulose ethers, cellulose esters, gelatin, pharmaceutical glaze, polyethylene glycol, polyvinyl acetate phthalate, sucrose, carnauba wax, microcrystalline wax, (meth)acrylic acid/(meth)acrylic ester copolymers, and other vinylic polymers and copolymers.

12. The process of claim 11 wherein the residual solvent is extracted from film coated tablets.

13. The process of claim 11 wherein said residual solvent is extracted from oral osmotic systems.

14. The process of claim 13 wherein the residual solvent is extracted from oral osmotic systems containing metoprolol fumarate, dextromethorphan hydrobromide, or phenylpropanolamine hydrochloride.

15. The process of claim 11 wherein organic solvents are extracted.

16. The process of claim 11 wherein methylene chloride and/or methanol are the solvent which are extracted.

17. The process of claim 11 wherein said article is a film coated tablet and said inert phase of gas under near-critical conditions is an inert phase of a material selected from the group consisting of carbon dioxide and nitrous oxide.

18. The process of claim 17 wherein the solvent is extracted from tablets coated with cellulose esters.

19. The process of claim 11 wherein said solvent is extracted from oral osmotic systems coated with cellulose esters.

20. A process for extracting residual solvent from a solid article selected from the group consisting of capsules and film coated tablets, said process comprising exposing that solid article to an inert phase of a gas under near-critical conditions, transferring a portion of the residual solvent from the solid article to the inert phase of the gas and removing the inert phase enriched with solvent from the solid article depleted of solvent, wherein said film coated tablets have a film coating comprising a film-forming member selected from the group consisting of cellulose ethers, cellulose esters, gelatin, pharmaceutical glaze, polyethylene glycol, polyvinyl acetate phthalate, sucrose, carnauba wax, microcrystalline wax, (meth)acrylic acid/(meth)acrylic ester copolymers, and other vinylic polymers and copolymers.

* * * * *